US008263137B2

(12) United States Patent
Squashic et al.

(10) Patent No.: US 8,263,137 B2
(45) Date of Patent: Sep. 11, 2012

(54) NUTRITIONAL SUPPLEMENT FOR WOMEN

(75) Inventors: Steven A. Squashic, Scotch Plains, NJ (US); Kevin M. Hudy, Hoboken, NJ (US); David C. Purdy, Tinton Falls, NJ (US)

(73) Assignee: Vertical Pharmaceuticals, Inc., Sayreville, NJ (US)

( * ) Notice: Subject to any disclaimer, the term of this patent is extended or adjusted under 35 U.S.C. 154(b) by 1183 days.

(21) Appl. No.: 12/053,073

(22) Filed: Mar. 21, 2008

(65) Prior Publication Data

US 2008/0226746 A1    Sep. 18, 2008

Related U.S. Application Data

(63) Continuation-in-part of application No. 11/197,760, filed on Aug. 4, 2005, now Pat. No. 7,998,500.

(51) Int. Cl.
*A61K 33/34* (2006.01)
*A23L 1/31* (2006.01)

(52) U.S. Cl. ........................ 424/630; 426/648

(58) Field of Classification Search .................. None
See application file for complete search history.

(56) References Cited

U.S. PATENT DOCUMENTS

| | | | |
|---|---|---|---|
| 4,582,709 A | 4/1986 | Peters et al. | |
| 4,629,625 A | 12/1986 | Gaull | |
| 4,752,479 A | 6/1988 | Briggs et al. | |
| 4,786,510 A | 11/1988 | Nakel et al. | |
| 4,786,518 A | 11/1988 | Nakel et al. | |
| 4,812,303 A | 3/1989 | Iorio | |
| 4,867,989 A | 9/1989 | Silva et al. | |
| 4,973,467 A | 11/1990 | Sahley | |
| 4,980,168 A | 12/1990 | Sahley | |
| 4,992,282 A | 2/1991 | Mehansho et al. | |
| 4,994,283 A | 2/1991 | Mehansho et al. | |
| 5,021,424 A | 6/1991 | Lawton-Wall | |
| 5,051,258 A | 9/1991 | Sahley | |
| 5,061,723 A | 10/1991 | Barua et al. | |
| 5,151,274 A | 9/1992 | Saltman et al. | |
| 5,223,285 A | 6/1993 | DeMichele et al. | |
| 5,308,627 A | 5/1994 | Umbdenstock, Jr. | |
| 5,312,626 A | 5/1994 | Gergely et al. | |
| 5,332,579 A | 7/1994 | Umbdenstock | |
| 5,445,837 A | 8/1995 | Burkes et al. | |
| 5,447,732 A | 9/1995 | Tanimoto et al. | |
| 5,468,506 A | 11/1995 | Andon | |
| 5,494,678 A | 2/1996 | Paradissis et al. | |
| 5,496,567 A | 3/1996 | McLean | |
| 5,501,857 A | 3/1996 | Zimmer | |
| 5,514,382 A | 5/1996 | Sultenfuss | |
| 5,569,458 A | 10/1996 | Greenberg | |
| 5,569,459 A | 10/1996 | Shlyankevich | |
| 5,569,477 A | 10/1996 | Nesbitt | |
| 5,571,441 A | 11/1996 | Andon et al. | |
| 5,597,585 A | 1/1997 | Williams et al. | |
| 5,612,061 A | 3/1997 | Rabkin | |
| 5,614,553 A | 3/1997 | Ashmead et al. | |
| 5,626,883 A | 5/1997 | Paul | |
| 5,646,116 A | 7/1997 | Burk | |
| 5,654,011 A | 8/1997 | Jackson et al. | |
| 5,686,107 A | 11/1997 | Ratnaraj et al. | |
| D393,203 S | 4/1998 | Saltzman et al. | |
| 5,770,215 A | 6/1998 | Moshyedi | |
| 5,807,586 A | 9/1998 | Jackson et al. | |
| 5,869,084 A | 2/1999 | Paradissis et al. | |
| 5,879,698 A | 3/1999 | Ellenbogen et al. | |
| 5,922,361 A | 7/1999 | Bieser et al. | |
| 5,922,704 A | 7/1999 | Bland | |
| 5,935,610 A | 8/1999 | McLean | |
| 5,948,443 A | 9/1999 | Riley et al. | |
| 5,952,317 A | 9/1999 | Deluca et al. | |
| 5,962,030 A | 10/1999 | Fine | |
| 5,965,162 A | 10/1999 | Fuisz et al. | |
| 5,976,568 A | 11/1999 | Riley | |
| 5,976,784 A | 11/1999 | Deluca et al. | |
| 5,977,073 A | 11/1999 | Khaled | |
| 6,040,333 A | 3/2000 | Jackson | |
| 6,051,236 A | 4/2000 | Portman | |
| 6,060,093 A | 5/2000 | Davis et al. | |
| 6,080,431 A | 6/2000 | Andon et al. | |
| 6,080,788 A | 6/2000 | Sole et al. | |
| 6,086,915 A | 7/2000 | Zeligs et al. | |
| 6,106,874 A | 8/2000 | Liebrecht et al. | |
| 6,124,268 A | 9/2000 | Ghosal | |
| 6,143,300 A | 11/2000 | Stevenot | |
| 6,150,399 A | 11/2000 | Patel et al. | |
| 6,150,411 A | 11/2000 | Stordy | |
| 6,174,857 B1 | 1/2001 | Burk | |
| 6,174,890 B1 | 1/2001 | Riga et al. | |
| 6,187,318 B1 | 2/2001 | Mitchell et al. | |
| 6,190,693 B1 | 2/2001 | Kafrissen et al. | |
| 6,197,329 B1 | 3/2001 | Hermelin et al. | |
| 6,203,819 B1 | 3/2001 | Fine | |
| 6,210,686 B1 | 4/2001 | Bell et al. | |

(Continued)

OTHER PUBLICATIONS

Howard C. Ansel et al., "Pharmaceutical Dosage Forms and Drug Delivery Systems," 1999, 7th Ed., Lippincott Williams & Wilkins; pp. 90-91, 179, and 346-348, 8 pages.
Alan H. Pressman, D.C. "The Complete Idiot's Guide to Vitamins and Minerals," 1997, NY, pp. 5, 7, 8, 20, 25, 46-50, 289 and 293, 14 pages.
Magnesium Factsheet, [online] Office of Dietary Supplements, National Institute of Health, Jan. 2005, Retrieved from the internet Jul. 7, 2009,http://web.archive.org/web/20050212015808/http://ods.od.nih.gov/factsheets/magnesium.asp, 13 pages.

*Primary Examiner* — David J Blanchard
*Assistant Examiner* — Garen Gotfredson
(74) *Attorney, Agent, or Firm* — Maldjian Law Group LLC; John P. Maldjian, Esq.

(57) ABSTRACT

A nutritional supplement comprising a variety of vitamins and minerals is described. A nutritional supplement comprising between about 1 mg and about 5 mg of vitamin $B_1$, between about 2 mg and about 8 mg of vitamin $B_2$, between about 7 mg and about 30 mg of vitamin $B_6$, between about 10 mcg and about 40 mcg of vitamin $B_{12}$, between about 1 mg and about 4 mg of folic acid, between about 250 IU and about 900 IU of vitamin $D_3$, between about 100 mg and about 400 mg of vitamin C, between about 20 IU and about 90 IUs of vitamin E, between about 0.5 mg and about 4 mg of copper, between about 20 mg and about 80 mg of zinc, between about 10 mg and about 70 mg of iron, and between about 100 mg and about 800 mg of omega-3 fatty acids is disclosed.

19 Claims, No Drawings

U.S. PATENT DOCUMENTS

| | | |
|---|---|---|
| 6,228,388 B1 | 5/2001 | Paradissis et al. |
| 6,235,322 B1 | 5/2001 | Lederman |
| 6,238,672 B1 | 5/2001 | Chen |
| 6,241,997 B1 | 6/2001 | Kershman et al. |
| 6,245,378 B1 | 6/2001 | Cavazza |
| 6,248,909 B1 | 6/2001 | Akimoto et al. |
| 6,255,341 B1 | 7/2001 | DeMichele et al. |
| 6,258,846 B1 | 7/2001 | Hermelin et al. |
| 6,261,600 B1 | 7/2001 | Kirschner et al. |
| 6,265,438 B1 | 7/2001 | Steward |
| 6,277,396 B1 | 8/2001 | Dente |
| 6,290,974 B1 | 9/2001 | Swaisgood et al. |
| 6,291,517 B1 | 9/2001 | Bagchi et al. |
| 6,291,533 B1 | 9/2001 | Fleischner |
| 6,299,886 B1 | 10/2001 | Piper |
| 6,299,896 B1 | 10/2001 | Cooper et al. |
| 6,300,309 B1 | 10/2001 | Guler et al. |
| 6,346,284 B1 | 2/2002 | Briend et al. |
| 6,352,713 B1 | 3/2002 | Kirschner et al. |
| 6,358,544 B1 | 3/2002 | Henry, Jr. et al. |
| 6,358,925 B1 | 3/2002 | Guler et al. |
| 6,361,800 B1 | 3/2002 | Cooper et al. |
| 6,362,221 B1 | 3/2002 | Clark et al. |
| 6,365,176 B1 | 4/2002 | Bell et al. |
| 6,368,640 B1 | 4/2002 | Wuh et al. |
| 6,369,042 B1 | 4/2002 | Oberthür et al. |
| 6,372,782 B1 | 4/2002 | Patel et al. |
| 6,410,058 B2 | 6/2002 | Gohlke et al. |
| 6,416,737 B1 | 7/2002 | Manolagas et al. |
| 6,420,350 B1 | 7/2002 | Fleischner |
| 6,426,097 B2 | 7/2002 | Grose |
| 6,432,442 B1 | 8/2002 | Buehler et al. |
| 6,436,406 B1 | 8/2002 | Yegorova |
| 6,436,453 B1 | 8/2002 | Van Lengerich et al. |
| 6,436,910 B1 | 8/2002 | Yerxa et al. |
| 6,440,450 B1 | 8/2002 | Han et al. |
| 6,444,218 B2 | 9/2002 | Han et al. |
| 6,447,809 B1 | 9/2002 | Krumhar et al. |
| 6,451,341 B1 | 9/2002 | Slaga et al. |
| 6,455,068 B1 | 9/2002 | Licari |
| 6,455,714 B1 | 9/2002 | Holick et al. |
| 6,461,652 B1 | 10/2002 | Henry et al. |
| 6,465,013 B1 | 10/2002 | DeBernardi |
| 6,468,568 B1 | 10/2002 | Leusner et al. |
| 6,475,511 B2 | 11/2002 | Gohlke et al. |
| 6,475,539 B1 | 11/2002 | DeWille et al. |
| 6,479,545 B1 | 11/2002 | Levinson et al. |
| 6,485,738 B1 | 11/2002 | Huang et al. |
| 6,488,956 B1 | 12/2002 | Paradissis et al. |
| 6,495,173 B1 | 12/2002 | Yegorova |
| 6,495,177 B1 | 12/2002 | deVries et al. |
| 6,495,736 B1 | 12/2002 | Brunkow et al. |
| 6,497,885 B2 | 12/2002 | Trant |
| 6,497,906 B1 | 12/2002 | Kelly |
| 6,503,529 B1 | 1/2003 | Fleischner |
| 6,509,045 B2 | 1/2003 | Henry et al. |
| 6,509,326 B1 | 1/2003 | Andon et al. |
| 6,517,861 B2 | 2/2003 | Singh et al. |
| 6,521,247 B1 | 2/2003 | deVries |
| 6,541,005 B1 | 4/2003 | Yegorova |
| 6,541,006 B1 | 4/2003 | Yegorova |
| 6,544,525 B1 | 4/2003 | Yegorova |
| 6,544,563 B2 | 4/2003 | Wuh et al. |
| 6,562,378 B1 | 5/2003 | Chandra |
| 6,565,891 B1 | 5/2003 | Chandra |
| 6,569,445 B2 | 5/2003 | Manning et al. |
| 6,569,477 B2 | 5/2003 | Lederman |
| 6,569,857 B1 | 5/2003 | Hermelin et al. |
| 6,569,869 B2 | 5/2003 | Assmann et al. |
| 6,576,242 B1 | 6/2003 | Yegorova |
| 6,576,253 B2 | 6/2003 | Manning et al. |
| 6,576,666 B2 | 6/2003 | Hermelin et al. |
| 6,579,544 B1 | 6/2003 | Rosenberg et al. |
| 6,579,899 B1 | 6/2003 | Wurtman et al. |
| 6,585,998 B2 | 7/2003 | Cartwright et al. |
| 6,592,863 B2 | 7/2003 | Fuchs et al. |
| 6,592,909 B2 | 7/2003 | Belcheff |
| 6,593,310 B1 | 7/2003 | Cullis-Hill |
| 6,596,313 B2 | 7/2003 | Rosenbloom |
| 6,596,762 B2 | 7/2003 | Sokol |
| 6,605,646 B2 | 8/2003 | Herbert |
| 6,630,158 B2 | 10/2003 | Popp et al. |
| 6,642,212 B1 | 11/2003 | Kelly |
| 6,646,013 B1 | 11/2003 | Barker et al. |
| 6,649,195 B1 * | 11/2003 | Gorsek ......................... 424/732 |
| 6,653,332 B2 | 11/2003 | Jaen et al. |
| 6,660,293 B2 | 12/2003 | Giordano et al. |
| 6,667,063 B2 | 12/2003 | Crum |
| 6,706,478 B2 | 3/2004 | Duff et al. |
| 6,720,013 B2 | 4/2004 | Johnson et al. |
| 6,743,770 B2 | 6/2004 | Bell et al. |
| 6,752,986 B2 | 6/2004 | Bauer et al. |
| 6,756,401 B2 | 6/2004 | Day et al. |
| 6,780,438 B2 | 8/2004 | Gohlke et al. |
| 6,790,462 B2 | 9/2004 | Hendricks |
| 6,793,935 B2 | 9/2004 | Hermelin et al. |
| 6,814,983 B2 | 11/2004 | Giordano et al. |
| 6,818,228 B1 | 11/2004 | Walsdorf et al. |
| 6,818,234 B1 | 11/2004 | Nair et al. |
| 6,827,945 B2 | 12/2004 | Rosenbloom |
| 6,830,761 B1 | 12/2004 | Zlotkin |
| 6,835,402 B1 | 12/2004 | Clark et al. |
| 6,837,682 B2 | 1/2005 | Evenson et al. |
| 6,843,372 B2 | 1/2005 | Weinstein |
| 6,844,012 B1 | 1/2005 | Forceville et al. |
| 6,849,274 B1 | 2/2005 | Whittle |
| 6,849,613 B2 | 2/2005 | Prasad et al. |
| 6,852,335 B2 | 2/2005 | DeBernardi |
| 6,863,904 B2 | 3/2005 | Giordano et al. |
| 6,881,419 B2 | 4/2005 | Lovett |
| 6,881,425 B2 | 4/2005 | Pushpangadan et al. |
| 6,887,850 B2 | 5/2005 | Fuchs et al. |
| 6,914,073 B2 | 7/2005 | Boulos et al. |
| 6,929,807 B1 | 8/2005 | McAnalley et al. |
| 6,953,588 B2 | 10/2005 | Cooper et al. |
| 6,955,873 B1 | 10/2005 | Blum |
| 6,960,581 B2 | 11/2005 | Betageri et al. |
| 6,995,166 B1 | 2/2006 | Giordano et al. |
| 2001/0022980 A1 | 9/2001 | Bell et al. |
| 2001/0031283 A1 | 10/2001 | Belcheff |
| 2001/0031744 A1 | 10/2001 | Kosbab |
| 2001/0036468 A1 | 11/2001 | Han et al. |
| 2001/0036936 A1 | 11/2001 | Day et al. |
| 2001/0041741 A1 | 11/2001 | Sole et al. |
| 2001/0055623 A1 | 12/2001 | Jackson |
| 2002/0015762 A1 | 2/2002 | Quinlan |
| 2002/0032234 A1 | 3/2002 | Hermelin et al. |
| 2002/0034543 A1 | 3/2002 | Kirschner et al. |
| 2002/0037928 A1 | 3/2002 | Jaen et al. |
| 2002/0044957 A1 | 4/2002 | Fuchs et al. |
| 2002/0044961 A1 | 4/2002 | Kirschner et al. |
| 2002/0044988 A1 | 4/2002 | Fuchs et al. |
| 2002/0045184 A1 | 4/2002 | Chen |
| 2002/0058088 A1 | 5/2002 | Henry et al. |
| 2002/0064578 A1 | 5/2002 | Henry et al. |
| 2002/0066691 A1 | 6/2002 | Varon |
| 2002/0099032 A1 | 7/2002 | Higashi et al. |
| 2002/0102330 A1 | 8/2002 | Schramm et al. |
| 2002/0110604 A1 | 8/2002 | Babish et al. |
| 2002/0119183 A1 | 8/2002 | Hermelin et al. |
| 2002/0119928 A1 | 8/2002 | McAnalley |
| 2002/0119933 A1 | 8/2002 | Butler et al. |
| 2002/0132800 A1 | 9/2002 | Popp et al. |
| 2002/0136711 A1 | 9/2002 | Cochran |
| 2002/0136782 A1 | 9/2002 | Fleischner |
| 2002/0137749 A1 | 9/2002 | Levinson et al. |
| 2002/0146471 A1 | 10/2002 | Wuh et al. |
| 2002/0147152 A1 | 10/2002 | Bell et al. |
| 2002/0147153 A1 | 10/2002 | Bell et al. |
| 2002/0150607 A1 | 10/2002 | Schramm et al. |
| 2002/0150649 A1 | 10/2002 | Bell |
| 2002/0155163 A1 | 10/2002 | Benjamin et al. |
| 2002/0155181 A1 | 10/2002 | Wuh et al. |
| 2002/0168429 A1 | 11/2002 | Mann |
| 2002/0172721 A1 | 11/2002 | Boulos et al. |
| 2002/0173510 A1 | 11/2002 | Levinson et al. |
| 2002/0187205 A1 | 12/2002 | Paradissis et al. |

| | | |
|---|---|---|
| 2002/0193379 A1 | 12/2002 | Copp et al. |
| 2002/0197330 A1 | 12/2002 | Jackson et al. |
| 2003/0012824 A1 | 1/2003 | Ott et al. |
| 2003/0012826 A1 | 1/2003 | Giordano et al. |
| 2003/0013639 A1 | 1/2003 | Yurchak et al. |
| 2003/0017205 A1 | 1/2003 | DeBernardi |
| 2003/0031726 A1 | 2/2003 | Hendricks |
| 2003/0044473 A1 | 3/2003 | Fleischner |
| 2003/0059481 A1 | 3/2003 | Krumhar et al. |
| 2003/0068372 A1 | 4/2003 | Kirschner et al. |
| 2003/0091552 A1 | 5/2003 | Cartwright et al. |
| 2003/0091613 A1 | 5/2003 | DeWille et al. |
| 2003/0096018 A1 | 5/2003 | Schloss et al. |
| 2003/0099730 A1 | 5/2003 | Rosenbloom |
| 2003/0104050 A1 | 6/2003 | Matharu et al. |
| 2003/0104078 A1 | 6/2003 | Barrett-Reis et al. |
| 2003/0108594 A1 | 6/2003 | Manning et al. |
| 2003/0108605 A1 | 6/2003 | Hermelin et al. |
| 2003/0108624 A1 | 6/2003 | Kosbab |
| 2003/0138484 A1 | 7/2003 | Gianesello et al. |
| 2003/0143287 A1 | 7/2003 | Bell |
| 2003/0147996 A1 | 8/2003 | Prasad et al. |
| 2003/0148946 A1 | 8/2003 | Levy et al. |
| 2003/0162807 A1 | 8/2003 | Day et al. |
| 2003/0166247 A1 | 9/2003 | Brunkow et al. |
| 2003/0170327 A1 | 9/2003 | Dahl |
| 2003/0185918 A1 | 10/2003 | Rosenbloom |
| 2003/0190355 A1 | 10/2003 | Hermelin et al. |
| 2003/0190369 A1 | 10/2003 | Lovett |
| 2003/0198661 A1 | 10/2003 | Harper et al. |
| 2003/0198730 A1 | 10/2003 | Stewart |
| 2003/0202992 A1 | 10/2003 | Fuchs et al. |
| 2003/0203053 A1 | 10/2003 | Wuh et al. |
| 2003/0206969 A1 | 11/2003 | Nidamarty et al. |
| 2003/0216351 A1 | 11/2003 | Hermelin et al. |
| 2003/0229014 A1 | 12/2003 | Schneider et al. |
| 2004/0009535 A1 | 1/2004 | Brunkow et al. |
| 2004/0013743 A1 | 1/2004 | Jackson |
| 2004/0047898 A1 | 3/2004 | Harper et al. |
| 2004/0048812 A1 | 3/2004 | Kelly |
| 2004/0048870 A1 | 3/2004 | Amir et al. |
| 2004/0052918 A1 | 3/2004 | Briend et al. |
| 2004/0058321 A1 | 3/2004 | Brunkow et al. |
| 2004/0076664 A1 | 4/2004 | Bonura |
| 2004/0082536 A1 | 4/2004 | Cooper et al. |
| 2004/0086574 A1 | 5/2004 | Giordano et al. |
| 2004/0087515 A1 | 5/2004 | Butler et al. |
| 2004/0101554 A1 | 5/2004 | Kirschner et al. |
| 2004/0106561 A1 | 6/2004 | Kelly |
| 2004/0109901 A1 | 6/2004 | Giordano et al. |
| 2004/0140241 A1 | 7/2004 | Weinstein |
| 2004/0162292 A1 | 8/2004 | Evenstad et al. |
| 2004/0166175 A1 | 8/2004 | Giordano et al. |
| 2004/0170702 A1 | 9/2004 | VanStockum |
| 2004/0175415 A1 | 9/2004 | Chan et al. |
| 2004/0185119 A1 | 9/2004 | Theuer |
| 2004/0191296 A1 | 9/2004 | Sternberg |
| 2004/0197430 A1 | 10/2004 | Meyrowitz |
| 2004/0198674 A1 | 10/2004 | Levy et al. |
| 2004/0209848 A1 | 10/2004 | Maruyama et al. |
| 2004/0213857 A1 | 10/2004 | Soldati et al. |
| 2004/0213873 A1 | 10/2004 | Parvez |
| 2004/0219235 A1 | 11/2004 | Pushpangadan et al. |
| 2004/0220118 A1 | 11/2004 | Bland et al. |
| 2004/0224032 A1 | 11/2004 | Zlotkin |
| 2004/0228931 A1 | 11/2004 | Chokshi et al. |
| 2004/0234544 A1 | 11/2004 | Jager et al. |
| 2004/0234579 A1 | 11/2004 | Finke |
| 2004/0235728 A1 | 11/2004 | Stoch et al. |
| 2004/0254095 A1 | 12/2004 | Martin et al. |
| 2004/0259886 A1 | 12/2004 | Day et al. |
| 2005/0009835 A1 | 1/2005 | Thomas |
| 2005/0016893 A1 | 1/2005 | Nakagawa et al. |
| 2005/0026223 A1 | 2/2005 | Manolagas et al. |
| 2005/0032741 A1 | 2/2005 | Venkataraman |
| 2005/0037065 A1 | 2/2005 | Kirschner et al. |
| 2005/0058671 A1 | 3/2005 | Bedding et al. |
| 2005/0059641 A1 | 3/2005 | Ray et al. |
| 2005/0069608 A1 | 3/2005 | Hendricks |
| 2005/0095262 A1 | 5/2005 | Camponovo et al. |
| 2005/0100613 A1 | 5/2005 | Giordano et al. |
| 2005/0101670 A1 | 5/2005 | Hermelin et al. |
| 2005/0106266 A1 | 5/2005 | Levinson et al. |
| 2005/0112176 A1 | 5/2005 | Dopson et al. |
| 2005/0112177 A1 | 5/2005 | Dopson et al. |
| 2005/0112211 A1 | 5/2005 | Gervais et al. |
| 2005/0119218 A1 | 6/2005 | Prasad et al. |
| 2005/0123628 A1 | 6/2005 | Zabrecky |
| 2005/0130933 A1 | 6/2005 | Jacobs et al. |
| 2005/0142124 A1 | 6/2005 | Kaiser |
| 2005/0143357 A1 | 6/2005 | Pousette et al. |
| 2005/0153019 A1 | 7/2005 | Fuchs et al. |
| 2005/0171034 A1 | 8/2005 | Halevie-Goldman |
| 2005/0186252 A1 | 8/2005 | Ahlgren et al. |
| 2005/0187144 A1 | 8/2005 | Fine et al. |
| 2005/0196343 A1 | 9/2005 | Reddy et al. |
| 2005/0196434 A1 | 9/2005 | Brierre |
| 2005/0196469 A1 | 9/2005 | Thys-Jacobs |
| 2005/0214383 A1 | 9/2005 | Bubnis et al. |
| 2005/0214388 A1 | 9/2005 | Gorham et al. |
| 2005/0226942 A1 | 10/2005 | Myhill et al. |
| 2005/0233946 A1 | 10/2005 | Fine et al. |
| 2005/0233947 A1 | 10/2005 | Fine et al. |
| 2005/0249787 A1 | 11/2005 | Reynolds et al. |
| 2005/0249788 A1 | 11/2005 | Reynolds et al. |
| 2005/0256178 A1 | 11/2005 | Eggersdorfer et al. |
| 2005/0260284 A1 | 11/2005 | Dimateeo-Leggio |
| 2005/0261172 A1 | 11/2005 | Schneider et al. |
| 2005/0261257 A1 | 11/2005 | Vermeer |
| 2005/0281888 A1 | 12/2005 | Chandra |
| 2005/0281889 A1 | 12/2005 | Chandra |
| 2005/0282794 A1 | 12/2005 | Fine et al. |
| 2005/0287228 A1 | 12/2005 | Trant |
| 2006/0003981 A1 | 1/2006 | Fine et al. |
| 2006/0008543 A1 | 1/2006 | Myhill et al. |
| 2006/0008544 A1 | 1/2006 | Myhill et al. |
| 2006/0018975 A1 | 1/2006 | Talbott |
| 2006/0024384 A1 | 2/2006 | Giordano |
| 2006/0024409 A1 | 2/2006 | Giordano |
| 2006/0034912 A1 | 2/2006 | Giordano et al. |
| 2006/0034916 A1 | 2/2006 | Giordano et al. |
| 2006/0160753 A1 * | 7/2006 | Cassidy et al. .................. 514/27 |

* cited by examiner

NUTRITIONAL SUPPLEMENT FOR WOMEN

CROSS-REFERENCE TO RELATED APPLICATIONS

This application is a continuation-in-part of U.S. patent application Ser. No. 11/197,760, filed Aug. 4, 2005, now U.S. Pat No. 7,998,500 the entirety of which is hereby incorporated by reference.

BACKGROUND

1. Field

Embodiments of the present invention generally relate to nutritional supplements and in particular to nutritional supplements for use by women.

2. Description of the Related Art

Nutrition plays a critical role in maintaining good health, especially in women during child-bearing years. Prescription multi-vitamin/multi-mineral nutritional supplements are often needed for improving the nutritional status of women prior to conception, throughout pregnancy and in the postnatal period for both lactating and non-lactating mothers. Pregnancy and lactation are among the most nutritionally volatile and physiologically stressful periods in the lifetime of a woman.

Specifically, vitamin and mineral needs are almost universally increased during these natural processes. These increased needs are almost always due to elevated metabolic demand, increased plasma volume, increased levels of blood cells, decreased concentrations of nutrients, and decreased concentrations of nutrient-binding proteins.

Research has suggested that optimizing specific nutrients before, during and after physiological processes of pregnancy and lactation can have a profound, positive and comprehensive impact upon the overall wellness of the mother and of the developing and newborn child, as well as the safety and health of the mother.

Thus, there is a need for a nutritional supplement to be used in improving the nutritional condition of women prior to conception, throughout pregnancy and in the postnatal period for both lactating and non-lactating mothers.

SUMMARY

Embodiments of the present invention relate to nutritional supplements for women during pre-pregnancy and post-pregnancy in both lactating and non-lactating conditions. The nutritional supplement comprises a source of vitamin $B_1$, a source of vitamin $B_2$, a source of vitamin $B_6$, a source of vitamin $B_{12}$, folic acid, vitamin $D_3$, vitamin C, and vitamin E; a source of minerals including copper, magnesium, zinc and iron; and a source of essential omega-3 fatty acids, such as docosahexaenoic acid (DHA) and eicosapentaenoic acid (EPA).

The nutritional supplement can be made in a variety of forms, including a pill, a tablet, a caplet, a capsule, a chewable tablet, a quick dissolve tablet, an effervescent tablet, a hard gelatin capsule, a soft gelatin capsule, a powder, a liquid suspension, a food product, and any other form feasible in the context of the present invention. One of ordinary skill in the art would recognize there are also other viable ways for delivering the nutritional supplement to a user.

In one embodiment, a nutritional supplement composition comprises between about 1 mg and about 5 mg of vitamin $B_1$, between about 2 mg and about 8 mg of vitamin $B_2$, between about 7 mg and about 30 mg of vitamin $B_6$, between about 10 mcg and about 40 mcg of vitamin $B_{12}$, between about 1 mg and about 4 mg of folic acid, between about 250 IU and about 900 IU of vitamin $D_3$, between about 100 mg and about 400 mg of vitamin C, between about 20 IU and about 90 IUs of vitamin E, between about 0.5 mg and about 4 mg of copper, between about 20 mg and about 80 mg of zinc, between about 10 mg and about 70 mg of iron, and between about 100 mg and about 800 mg of omega-3 fatty acids.

In another embodiment, a nutritional supplement composition comprises about 2 mg of vitamin $B_1$, about 3.4 mg of vitamin $B_2$, about 10 mg of vitamin $B_6$, about 15 mcg of vitamin $B_{12}$, about 1.25 mg of folic acid, about 400 IU of vitamin $D_3$, about 120 mg of vitamin C, about 30 IU of vitamin E, about 1 mg of copper, about 25 mg of zinc, about 28 mg of iron, and about 200 mg of omega-3 fatty acids.

In yet another embodiment, a method comprises the step of administering to an individual a composition comprising between about 2 mg and about 4 mg of vitamin $B_1$, between about 3.4 mg and about 6.8 mg of vitamin $B_2$, between about 10 mg and about 20 mg of vitamin $B_6$, between about 15 mcg and about 30 mcg of vitamin $B_{12}$, between about 1.25 mg and about 2.50 mg of folic acid, between about 400 IU and about 800 IU of vitamin $D_3$, between about 120 mg and about 240 mg of vitamin C, between about 30 IU and about 60 IUs of vitamin E, between about 1 mg and about 2 mg of copper, between about 25 mg and about 50 mg of zinc, between about 28 mg and about 56 mg of iron, and between about 200 mg and about 400 mg of omega-3 fatty acids.

DETAILED DESCRIPTION

It is understood that the embodiments of the present invention are not limited to the particular methodologies, protocols, solvents and reagents, and the like, described herein as they may vary. It is also to be understood that the terminology used herein is used for the purpose of describing particular embodiments only and not intended to limit the scope of the present invention. It must also be noted that, as used herein and in the appended claims, the singular forms "a," "an" and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meaning as commonly understood by one of ordinary skill in the art to which this invention pertains. Preferred methods, devices and materials are described, although any methods and materials similar or equivalent to those described herein could be used in the practice or testing of the present invention. All references cited herein are incorporated by reference herein in their entirety.

The term "disease state," as used herein, may comprise any state in which one or more organs or components of an organism malfunction. The term "disease state" may refer to any deterioration of any component of a body. The term "disease state" may refer to any deficiency of any element, ion, molecule, atom, or compound necessary for the maintenance or function of any component of any organism. The term "disease state" may refer to any condition in which a body contains toxins, produced by microorganisms that infect the body or by body cells through faulty metabolism or absorbed from an external source.

The term "disease states" may be adverse states caused by any diet, any virus, or any bacteria. "Disease states" may comprise disorders associated with pregnant females such as, for example, osteomalacia and pre-eclampsia and disorders associated with a fetus such as, for example, neurotube defects and various fetal abnormalities. "Disease states" may comprise any pulmonary disorder such as, for example, bronchitis, bronchiectasis, atelectasis, pneumonia, diseases caused by inorganic dust, diseases caused by organic dust, any pulmonary fibrosis, and pleurisy. "Disease states" may comprise any hematological/oncological disorders such as, for example, anemia, hemophilia, leukemia, or lymphoma.

A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, Acquired Immune Deficiency Syndrome (AIDS), AIDS-related complex, infection by any strain of any Human Immunodeficiency Virus (HIV), and other viruses and pathogens such as bacteria.

A "disease state" may comprise any cardiovascular disorders such as, for example, arterial hypertension, orthostatic hypotension, arteriolosclerosis, coronary artery disease, cardiomyopathy, any arrhythmia, any valvular heart disease, endocarditis, pericardial disease, any cardiac tumor, any aneurism, and any peripheral vascular disorder. "Disease states" may comprise any hepatic/biliary disorders such as, for example, jaundice, hepatic steatosis, fibrosis, cirrhosis, hepatitis, any hepatic granuloma, any liver tumor, cholelithiasis, cholecystitis, and choledocholithiasis.

The term "physiologically stressful state," as used herein, comprises any state of an organism in which the organism faces one or more physiological challenges. A "physiologically stressful state" may comprise pre-pregnancy, pregnancy, lactation, or conditions in which an organism faces physiological challenges related to for example, elevated metabolic demand, increased plasma volume, or decreased concentrations of nutrient-binding proteins. A "physiologically stressful state" may result from one or more disease states.

The term "subject" as used herein comprises any and all organisms and includes the term "patient." "Subject" may refer to a human or any other animal. "Subject" may also refer to a fetus.

Proper nutrition is essential for maintaining health and preventing diseases. Adequate nutrition is especially critical during, for example, nutritionally volatile or physiologically stressful periods, such as periods comprising pre-pregnancy, pregnancy, lactation, or a disease state. Vitamin and mineral needs are almost universally increased throughout these periods. Increased needs during physiologically stressful states such as pre-pregnancy, pregnancy, or lactation, for example, may result from elevated metabolic demand, increased plasma volume, increased quantities of circulating red blood cells, decreased concentrations of nutrients, and decreased concentrations of nutrient-binding proteins, such as serum ferritin, maltose-binding protein, lactoferrin, calmodulin, tocopheryl binding protein, riboflavin binding protein, retinal binding protein, transferrin, high density lipoprotein-apolipoprotein A1, folic acid binding protein, and 25-hydroxy-vitamin D binding protein.

In one embodiment, the nutritional supplement comprises between about 0.5 mg and about 5 mg of vitamin $B_1$, between about 1.0 mg and about 10 mg of vitamin $B_2$, between about 5 mg and about 50 mg of vitamin $B_6$, between about 5 mcg and about 50 mcg of vitamin $B_{12}$, between about 0.5 mg and about 5.0 mg of folic acid, between about 100 IU and about 1,000 IU of vitamin $D_3$, between about 50 mg and about 500 mg of vitamin C, between about 10 IU and about 100 IUs of vitamin E, between about 0.25 mg and about 5 mg of copper, between about 10 mg and about 100 mg of zinc, between about 5 mg and about 75 mg of iron, and between about 50 mg and about 1,000 mg of omega-3 fatty acids.

In one embodiment, the nutritional supplement composition comprises between about 1 mg and about 5 mg of vitamin $B_1$, between about 2 mg and about 8 mg of vitamin $B_2$, between about 7 mg and about 30 mg of vitamin $B_6$, between about 10 mcg and about 40 mcg of vitamin $B_{12}$, between about 1 mg and about 4 mg of folic acid, between about 250 IU and about 900 IU of vitamin $D_3$, between about 100 mg and about 400 mg of vitamin C, between about 20 IU and about 90 IUs of vitamin E, between about 0.5 mg and about 4 mg of copper, between about 20 mg and about 80 mg of zinc, between about 10 mg and about 70 mg of iron, and between about 100 mg and about 800 mg of omega-3 fatty acids.

In another embodiment, the nutritional supplement comprises between about 2 mg and about 4 mg of vitamin $B_1$, between about 3.4 mg and about 6.8 mg of vitamin $B_2$, between about 10 mg and about 20 mg of vitamin $B_6$, between about 15 mcg and about 30 mcg of vitamin $B_{12}$, between about 1.25 mg and about 2.50 mg of folic acid, between about 400 IU and about 800 IU of vitamin $D_3$, between about 120 mg and about 240 mg of vitamin C, between about 30 IU and about 60 IUs of vitamin E, between about 1 mg and about 2 mg of copper, between about 25 mg and about 50 mg of zinc, between about 28 mg and about 56 mg of iron, and between about 200 mg and about 400 mg of omega-3 fatty acids.

In yet another embodiment, the nutritional supplement comprises about 2 mg of vitamin $B_1$, about 3.4 mg of vitamin $B_2$, about 10 mg of vitamin $B_6$, about 15 mcg of vitamin $B_{12}$, about 1.25 mg of folic acid, about 400 IU of vitamin $D_3$, about 120 mg of vitamin C, about 30 IU of vitamin E, about 1 mg of copper, about 25 mg of zinc, about 28 mg of iron, and about 200 mg of omega-3 fatty acids.

In another embodiment the inactive ingredients include croscarmellose sodium, microcrystalline cellulose, calcium phosphate, stearic acid, magnesium stearate, silica, povidone, hydroxypropyl methylcellulose, titanium dioxide, and FD&C red number 40.

The nutritional supplement can be made in a variety of forms, such as pharmaceutical compositions (e.g., tablet, powder, suspension, liquid, capsule, and gel), nutritional beverages, puddings, confections (e.g., candy), ice cream, frozen confections and novelties or non-baked, extruded food products such as bars.

In another embodiment, the ingredients of the nutritional supplement can be administered separately, just by incorporating certain components (e.g., bitter tasting ones) into a capsule or tablet and the remaining ingredients provided as a powder or nutritional bar. One form of a nutritional supplement tablet comprises a multi-vitamin/mineral with iron, specially formulated for women during pre-pregnancy, during pregnancy and during post-pregnancy. The nutritional supplement can be formulated for single or multiple daily administration, preferably one bisected tablet daily or as otherwise prescribed by a physician.

The embodiments of the present invention further pertain to therapeutic methods for managing nutrition of women during pre-pregnancy, pregnancy and post-pregnancy. The nutritional supplement can be administered to a woman to mitigate nutritional deficiencies and increase the healthiness of an unborn, a newborn, and/or the mother.

Vitamin A is a family of fat-soluble compounds that play an important role in vision, bone growth, reproduction, cell division, and cellular differentiation (the process whereby a nonspecialized cell acquires a specialized function, such as becoming a lung cell, brain cell, blood cell, etc.). Vitamin A helps regulate the immune system, which helps prevent and fight off infections by making white blood cells that destroy harmful bacteria and viruses. Vitamin A also may help lymphocytes, a type of white blood cell, to fight infections more effectively. Vitamin A promotes healthy surface linings of the eyes and the respiratory, urinary, and intestinal tracts. When those linings break down, it becomes easier for bacteria to enter the body and cause infection. Vitamin A also helps to maintain the integrity of skin and mucous membranes, which also function as a barrier to bacteria and viruses.

Vitamin E, a fat-soluble group of vitamins, is a group of antioxidants involved in the metabolism of all cells. Vitamin E protects vitamin A and essential fatty acids from oxidation in the body cells and prevents breakdown of body tissues. Vitamers of vitamin E include tocopherols and tocotrienols.

Vitamin $D_3$, also known as cholecalciferol, is a naturally-occurring bodily substance that many believe exert a protective effect in multiple sclerosis—both in the development of the disease and in limiting its progression. It is naturally produced in the skin in response to sunlight, but is also present in certain foodstuffs (particularly oily fish). Vitamin $D_3$ is structurally similar to members of the steroid family and, among other things, is a powerful mediator of immune function.

Vitamin $D_3$ is best known for its effects on calcium metabolism. Proper levels are necessary to maintain bone mineral density and serum (blood plasma) calcium levels. This is especially true among the very young where it is used to treat rickets, and utilized in combination with vitamin A for the treatment of osteoporosis in the elderly, particularly postmenopausal women who are often subject to fractures due to loss of bone density.

In studies, vitamin $D_3$ has been found helpful against autoimmunity for the downregulation of Th1 and upregulation of Th2 cells. It has also been shown to regulate the neurotrophins NGF (nerve growth factor), NT-3 (neurotrophin-3) and NT-4 (neurotrophin-4). In addition, vitamin $D_3$ has also been found to promote cellular differentiation, and cell death in neuroblastoma (brain tumor) cell lines, as well as in cancers in general.

Vitamin C is a water-soluble, antioxidant vitamin. It is important in forming collagen, a protein that gives structure to bones, cartilage, muscle, and blood vessels. Vitamin C also aids in the absorption of iron, and helps maintain healthy capillaries, bones, and teeth. As a water-soluble antioxidant, vitamin C is in a unique position to "scavenge" aqueous peroxyl radicals before these destructive substances have a chance to damage lipids. It works along with vitamin E, a fat-soluble antioxidant, and the enzyme glutathione peroxidase to stop free radical chain reactions. Vitamin C can enhance the body's resistance to an assortment of diseases, including infectious diseases and many types of cancer. It strengthens and protects the immune system by stimulating the activity of antibodies and immune system cells such as phagocytes and neutrophils. Vitamin C also contributes to a variety of other biochemical functions. These include the biosynthesis of the amino acid carnitine and the catecholamines that regulate the nervous system. It also helps the body to absorb iron and to break down histamine. Although vitamin C is found in every cell, it is especially useful in key parts of the body, including the blood, the skin, the nervous system, the teeth, the bones, and glands such as the thymus, adrenal glands and thyroid.

Vitamin $B_1$, also known as thiamine, helps to fuel your body by converting blood sugar into energy. It keeps the mucous membranes healthy and is essential for nervous system, cardiovascular and muscular function. Vitamin $B_1$ is essential for the metabolism of carbohydrates to produce energy, and for normal nerve and heart function.

Vitamin $B_3$, also known as niacin, is required for cell respiration, helps in the release of energy and metabolism of carbohydrates, fats, and proteins, proper circulation and healthy skin, functioning of the nervous system, and normal secretion of bile and stomach fluids. It is also used in the synthesis of sex hormones, treatment of schizophrenia and other mental illnesses, and as a memory enhancer. Niacin, given in a pharmaceutical dosage, improves the blood cholesterol profile, and has been used to clear the body of organic poisons, such as certain insecticides.

Folic acid is a water-soluble vitamin in the B-complex group; it is also known as vitamin $B_9$. Folic acid works in conjunction with vitamin $B_{12}$ and vitamin C to help the body to digest and utilize proteins, and to synthesize new proteins when required. It is necessary for the production of red blood cells and for the synthesis of deoxyribonucleic acid (DNA). Folic acid also promotes tissue growth and normal cell function. In addition, it helps to increase appetite when needed, and stimulates the formation of digestive acids. Folic acid supplements may be used in the treatment of disorders associated with folic acid deficiency, and may also be part of the recommended treatment for certain menstrual problems and leg ulcers.

Vitamin $B_6$ is a water-soluble vitamin that exists in three major chemical forms: pyridoxine, pyridoxal, and pyridoxamine. It performs a wide variety of functions in the body and is essential for good health. For example, vitamin $B_6$ is needed to produce pyridoxal 5'-phosphate, which is a cofactor for metabolism in a great number of enzyme-catalyzed biochemical reactions. It is also essential for red blood cell metabolism. The nervous and immune systems need vitamin $B_6$ to function efficiently, and it is also needed for the conversion of tryptophan to niacin.

The body needs vitamin $B_6$ to make hemoglobin. Hemoglobin is an iron-containing protein found within red blood cells which carries oxygen to tissues throughout the body. Vitamin $B_6$ also helps increase the amount of oxygen carried by hemoglobin. A vitamin $B_6$ deficiency can result in a form of anemia that is similar to iron deficiency anemia.

Vitamin $B_6$ also helps maintain your blood glucose (sugar) level within a normal range. When caloric intake is low, your body needs vitamin $B_6$ to help convert stored carbohydrates or other nutrients to glucose in order to maintain normal blood sugar levels.

Vitamin $B_{12}$, a water-soluble vitamin, helps maintain healthy nerve cells and red blood cells. It is also needed to help make DNA, the genetic material found in all cells. Vitamers of vitamin $B_{12}$ include cyanocobalamin, hydroxocobalamin, methylcobalamin, and adenosylcobalamin, the root of which terms (i.e., "cobalamin") so named because they contain the metal cobalt.

Magnesium is the fourth most abundant mineral in the body and is essential to good health. Approximately 50% of total body magnesium is found in the bones. The other half is found predominantly inside cells of body tissues and organs. Only 1% of magnesium is found in blood, but the body works very hard to keep blood levels of magnesium constant. Magnesium is needed for more than 300 biochemical reactions in the body. It helps maintain normal muscle and nerve function, keeps heart rhythm steady, supports a healthy immune system, and keeps bones strong. Magnesium also helps regulate blood sugar levels, promotes normal blood pressure, and is known to be involved in energy metabolism and protein synthesis. Magnesium may also play a role in preventing and managing disorders such as hypertension, cardiovascular disease, and diabetes.

Zinc is vital for the healthy working of many of the body's systems. Zinc plays a crucial role in cell growth and cell division, where it is required for protein and DNA synthesis, in insulin activity, in the metabolism of the ovaries and testes, and in liver function. As a component of many enzymes, zinc is involved in the metabolism of proteins, carbohydrates, and lipids, and in the production of energy. Zinc helps with the healing of wounds and is a vital component of many enzymatic reactions. It is also important for healthy skin and is essential for a healthy immune system and resistance to infection.

Iron is an essential nutrient that carries oxygen and forms part of the oxygen-carrying proteins, hemoglobin in red blood cells and myoglobin in muscle. Iron is also a structural component at the catalytic site of a large number of enzymes covering a wide array of diverse metabolic functions. These include neurotransmitter synthesis and function, phagocyte antimicrobial activity, hepatic detoxification systems, and synthesis of DNA, collagen and bile acids.

Copper is needed for normal growth and health. Copper is also needed to help the body use iron. It is also important for nerve function, bone growth, and to help the body use sugar.

Omega-3 fatty acids are a class of polyunsaturated fatty acids, essential to healthy growth both in children and adults. Recent research has also shown that particular omega-3 fatty acids, such as docosahexaenoic acid (DHA) and eicosapentaenoic acid (EPA), may play a significant role in the prevention of coronary heart disease. Omega-3 fatty acids have also been linked to lowering blood pressure and reducing levels of unhealthy triglycerides and very low density lipoprotein (VLDL) cholesterol. Additionally, pregnant women who maintain healthy levels of omega-3 fatty acids, especially EPA and DHA, are shown to have a reduced risk of low birth weight and premature birth.

Further effects of omega-3 and omega-6 fatty acids are currently under study. Many believe omega-3 fatty acids such as DHA and EPA, in conjunction with omega-6 fatty acids, provide anti-inflammatory effects, which experts believe may lower the risk of ischemic and thrombotic stroke. Moreover, recent studies have shown that EPA and DHA have a significant effect on those with atherosclerosis, where those taking supplements of these omega-3 fatty acids experienced a significant decrease in thickness of the arteries, as well as increased blood flow.

In one embodiment, the nutritional supplement further comprises an additive, such as a dye. The additive may increase the aesthetic value of the nutritional composition, as well as provide a new functionality, either as an inert ingredient or as an active ingredient.

While the foregoing is directed to embodiments of the present invention, other and further embodiments of the invention may be devised without departing from the basic scope thereof.

What is claimed is:

1. A nutritional supplement composition consisting of:
 between about 1 mg and about 5 mg of vitamin $B_1$;
 between about 2 mg and about 8 mg of vitamin $B_2$;
 between about 7 mg and about 30 mg of vitamin $B_6$;
 between about 10 mcg and about 40 mcg of vitamin $B_{12}$;
 between about 1 mg and about 4 mg of folic acid;
 between about 250 IU and about 900 IU of vitamin $D_3$;
 between about 100 mg and about 400 mg of vitamin C;
 between about 20 IU and about 90 IUs of vitamin E;
 between about 0.5 mg and about 4 mg of copper;
 between about 20 mg and about 80 mg of zinc;
 between about 10 mg and about 70 mg of iron; and
 between about 100 mg and about 800 mg of omega-3 fatty acids.

2. The composition of claim 1, wherein the nutritional supplement is administered in a form selected from the group consisting of a pill, a tablet, a caplet, a capsule, a chewable tablet, a quick dissolve tablet, a powder, an effervescent tablet, a hard gelatin capsule, and a soft gelatin capsule.

3. The composition of claim 2, wherein the nutritional supplement is administered in a form with an enteric coating.

4. The composition of claim 1, wherein vitamin $B_{12}$ is in the form of cyanocobalamin.

5. The composition of claim 1, wherein vitamin E is in the form of a tocopherol.

6. The composition of claim 1, wherein the nutritional supplement is administered in the form of a liquid suspension.

7. The composition of claim 1, wherein the nutritional supplement is administered in the form of a food product.

8. The composition of claim 1, wherein the omega-3 fatty acids comprise docosahexaenoic acid and eicosapentaenoic acid.

9. A nutritional supplement composition consisting of:
 about 2 mg of vitamin $B_1$;
 about 3.4 mg of vitamin $B_2$;
 about 10 mg of vitamin $B_6$;
 about 15 mcg of vitamin $B_{12}$;
 about 1.25 mg of folic acid;
 about 400 IU of vitamin $D_3$;
 about 120 mg of vitamin C;
 about 30 IU of vitamin E;
 about 1 mg of copper;
 about 25 mg of zinc;
 about 28 mg of iron; and
 about 200 mg of omega-3 fatty acids.

10. The composition of claim 9, wherein the nutritional supplement is administered in a form selected from the group consisting of a pill, a tablet, a caplet, a capsule, a chewable tablet, a quick dissolve tablet, a powder, an effervescent tablet, a hard gelatin capsule, and a soft gelatin capsule.

11. The composition of claim 10, wherein the nutritional supplement is administered in a form with an enteric coating.

12. The composition of claim 9, wherein the nutritional supplement is administered in the form of a liquid suspension.

13. The composition of claim 9, wherein the nutritional supplement is administered in the form of a food product.

14. The composition of claim 9, wherein vitamin $B_{12}$ is in the form of cyanocobalamin.

15. The composition of claim 9, wherein vitamin E is in the form of a tocopherol.

16. The composition of claim 9, wherein the omega-3 fatty acids comprise docosahexaenoic acid and eicosapentaenoic acid.

17. A method comprising the step of:
 administering to an individual a composition consisting of:
 between about 2 mg and about 4 mg of vitamin $B_1$;
 between about 3.4 mg and about 6.8 mg of vitamin $B_2$;
 between about 10 mg and about 20 mg of vitamin $B_6$;
 between about 15 mcg and about 30 mcg of vitamin $B_{12}$;
 between about 1.25 mg and about 2.50 mg of folic acid;
 between about 400 IU and about 800 IU of vitamin $D_3$;
 between about 120 mg and about 240 mg of vitamin C;
 between about 30 IU and about 60 IUs of vitamin E;
 between about 1 mg and about 2 mg of copper;
 between about 25 mg and about 50 mg of zinc;
 between about 28 mg and about 56 mg of iron; and between about 200 mg and about 400 mg of omega-3 fatty acids.

18. The method of claim 17, wherein the omega-3 fatty acids of the composition comprise docosahexaenoic acid and eicosapentaenoic acid.

19. A nutritional supplement composition consisting of:
between about 1 mg and about 5 mg of vitamin $B_1$;
between about 2 mg and about 8 mg of vitamin $B_2$;
between about 7 mg and about 40 mg of vitamin $B_6$;
between about 5 mcg and about 50 mcg of vitamin $B_{12}$;
between about 1 mg and about 4 mg of folic acid;
between about 250 IU and about 1000 IU of vitamin $D_3$;
between about 75 mg and about 400 mg of vitamin C;
between about 20 IU and about 90 IUs of vitamin E;
between about 0.5 mg and about 4 mg of copper;
between about 15 mg and about 80 mg of zinc;
between about 10 mg and about 70 mg of iron; and
between about 100 mg and about 800 mg of omega-3 fatty acids.

* * * * *